US010379065B2

(12) United States Patent
Preosti et al.

(10) Patent No.: US 10,379,065 B2
(45) Date of Patent: Aug. 13, 2019

(54) MEASURING METHOD AND DEVICE FOR MEASURING THE MOISTURE CONTENT, THE LENGTH AND/OR AT LEAST ONE DYNAMOMETRIC CHARACTERISTIC OF TEXTILE FIBERS, IN PARTICULAR COTTON FIBERS

(71) Applicant: MESDAN S.p.A., Puegnago Del Garda (IT)

(72) Inventors: Gianpiero Preosti, Salionze-Valeggio Sul Mincio (IT); Marco Musesti, Roe Volciano (IT)

(73) Assignee: MESDAN S.p.A., Puegnago Del Garda (IT)

( * ) Notice: Subject to any disclaimer, the term of this patent is extended or adjusted under 35 U.S.C. 154(b) by 180 days.

(21) Appl. No.: 15/334,999

(22) Filed: Oct. 26, 2016

(65) Prior Publication Data
US 2017/0122882 A1    May 4, 2017

(30) Foreign Application Priority Data

Oct. 30, 2015    (IT) .................. 102015000067599

(51) Int. Cl.
*G01N 3/00*    (2006.01)
*G01N 3/08*    (2006.01)
(Continued)

(52) U.S. Cl.
CPC .............. *G01N 22/04* (2013.01); *G01N 3/00* (2013.01); *G01N 33/365* (2013.01); *G01N 3/08* (2013.01)

(58) Field of Classification Search
CPC ............ G01N 22/04; G01N 3/00; G01N 3/08; G01N 33/365

(Continued)

(56) References Cited

U.S. PATENT DOCUMENTS 5,805,452 A * 9/1998 Anthony et al. ...... D01G 31/006
                                                        700/142
5,892,142 A * 4/1999 Ghorashi et al. .... G01N 33/362
                                                          73/38

(Continued)

FOREIGN PATENT DOCUMENTS

WO    WO 99/27353 A1    6/1999
WO    WO 00/14552    3/2000
WO    WO 2008/064497 A1    6/2008

OTHER PUBLICATIONS

Italian Search Report dated Apr. 8, 2016 in Italian Application UB20155168, filed Oct. 30, 2015 ( with English Translation of Categories of Cited Documents).

*Primary Examiner* — Jonathan M Dunlap
(74) *Attorney, Agent, or Firm* — Oblon, McClelland, Maier & Neustadt, L.L.P.

(57) ABSTRACT

A method for measuring the moisture content, the length and at least one dynamometric characteristic of textile fibers, includes pressing a layer of textile fibers between a pair of plates parallel to one another, withdrawing a line of textile fibers from said layer thus pressed and making the textile fibers of said line substantially coplanar and parallel to one another, bringing said line of textile fibers to a measuring area at which at least to perform one measuring step, moving the textile fibers away from the measuring area after having performed the at least one measuring step and measuring the moisture content of the textile fibers by means of microwave sensors.

27 Claims, 13 Drawing Sheets

(51) Int. Cl.
*G01N 22/04* (2006.01)
*G01N 33/36* (2006.01)

(58) Field of Classification Search
USPC .............................................. 73/73
See application file for complete search history.

(56) References Cited

U.S. PATENT DOCUMENTS

| | | | | |
|---|---|---|---|---|
| 5,907,394 A | * | 5/1999 | Ghorashi et al. ........ | G01N 3/08 356/73.1 |
| 5,943,907 A | * | 8/1999 | Ghorashi et al. ..... | G01N 33/362 19/66.1 |
| 6,025,724 A | | 2/2000 | Moshe et al. | |
| 6,098,454 A | * | 8/2000 | Ghorashi et al. ..... | G01N 33/362 73/160 |
| 6,112,131 A | | 8/2000 | Ghorashi et al. | |
| 6,204,670 B1 | | 3/2001 | Joshi | |
| 7,143,642 B1 | * | 12/2006 | Baxter et al. ......... | G01N 33/362 73/159 |
| 7,330,034 B1 | * | 2/2008 | Pelletier et al. ....... | G01N 22/04 324/634 |
| 7,845,054 B2 | * | 12/2010 | Schmitz et al. ..... | D01G 31/006 19/115 R |
| 2001/0030543 A1 | | 10/2001 | Joshi et al. | |

* cited by examiner

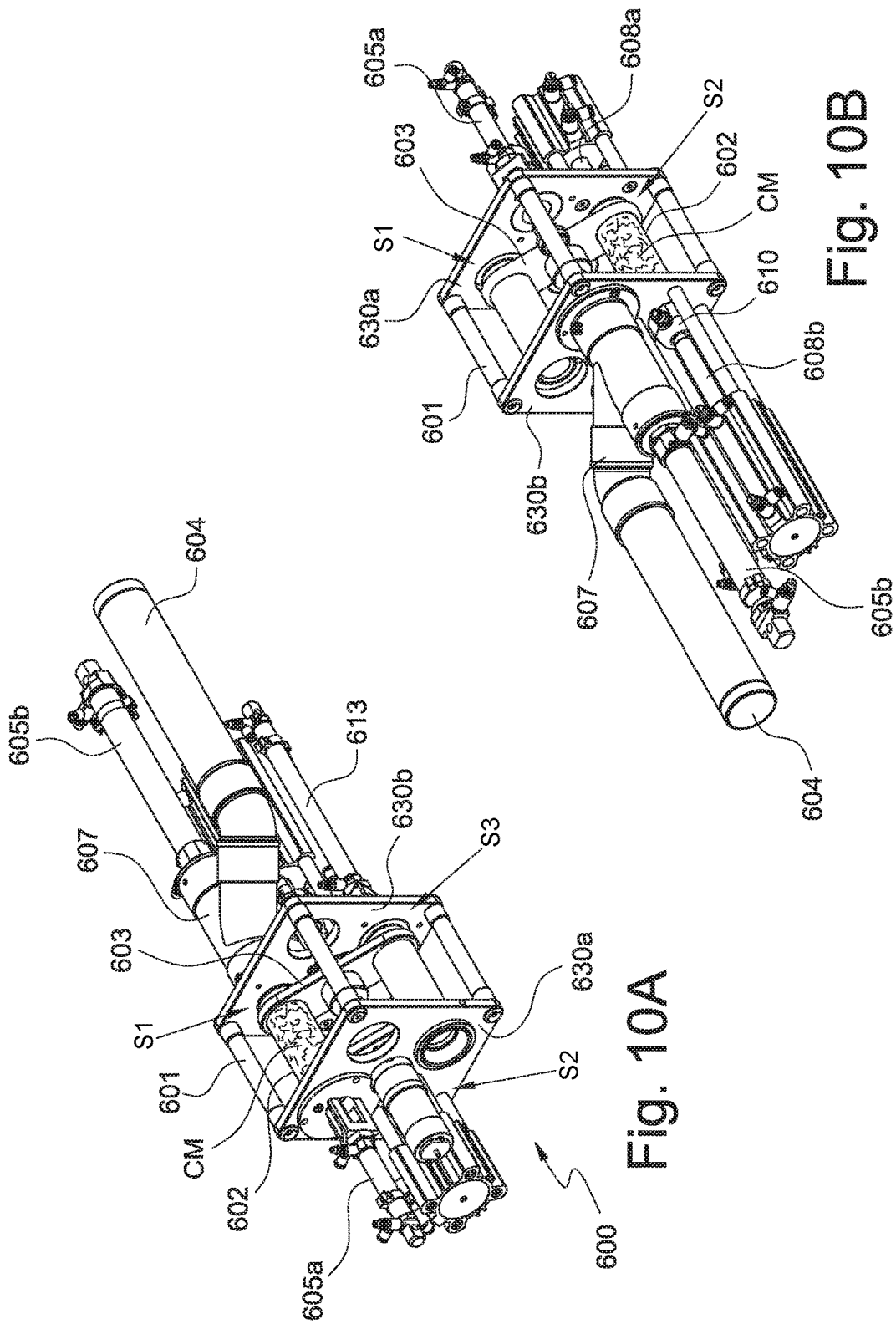

MEASURING METHOD AND DEVICE FOR MEASURING THE MOISTURE CONTENT, THE LENGTH AND/OR AT LEAST ONE DYNAMOMETRIC CHARACTERISTIC OF TEXTILE FIBERS, IN PARTICULAR COTTON FIBERS

The present invention relates to a measuring method and device for measuring the moisture content (i.e. the water content), the length and/or at least one dynamometric characteristic of textile fibers, in particular cotton fibers.

Numerous parameters are involved in determining the quality of cotton fibers and, therefore, in their classification according to classifications that are recognized by national or international entities and that determine, for example, their commercial value, processability or yield.

In general, the quality of cotton fibers is determined by the color, the content of imperfections, e.g. knots or neps of fibers, and of impurities, e.g. residues of insects or plant residues (seed fragments), by the degree of the stickiness ("cotton stickiness"), by the fineness/maturity of the fibers, by the moisture content, by the length and by the dynamometric characteristics (tensile stretching or elongation under tension before breaking and tensile strength, i.e. the maximum tensile stress that can be applied under tension before breaking).

Moreover, some of these characteristics are closely correlated to one another. In particular, it is known that the length and the dynamometric characteristics of cotton fibers vary, even markedly, as their moisture content (i.e. their water content) varies; for example, it has been observed that changes by one percentage point in moisture content entail changes by a few percentage points in length and in the dynamometric characteristics.

It is known that the length and the dynamometric characteristics of the cotton fibers are measured only after bringing the sample from which they are drawn to the conditions prescribed by the standards ("conditioning") so that, it is assumed, they will reach a defined moisture content.

For example, some standards (e.g. ASTM D-5867-12) prescribe maintaining the cotton fiber samples for at least 24 hours and up to 48 hours in an environment with a temperature of 21° C. and a moisture degree of 65%, conditioning at which it is assumed that the fiber sample will reach a uniform moisture content amounting to approximately 7%-8% by weight.

Moreover, not only is the moisture content of cotton fibers closely correlated to the conditions of the environment where they are located, but it changes the more rapidly, the lower their mass is; for example, a mass of cotton of approximately 70 mg, such as the one that is generally used in the form of a tuft or beard for length and/or dynamometric measurements, has reaction times to environmental changes and re-conditioning below 15 seconds.

However, it is not always possible to condition cotton fiber samples; for example, let us consider ginning plants where it is difficult to have the capability and interest in providing conditioning chambers, although it is necessary to determine the quality of the cotton fibers in this step of production as well.

Moreover, even if it is possible to condition cotton fiber samples to the conditions imposed by the standards, the moisture content assumed to have been reached may not be real.

Therefore, there are devices for measuring the moisture content of cotton fibers, which is then correlated to the measurements of the length and of the dynamometric characteristics of said fibers.

The most commonly known devices for measuring the moisture content of cotton fibers are of the resistive type and are based on the measurement of the electrical conductivity of a cotton fiber sample, conductivity that, as it is known, changes as the water content of the cotton fibers changes.

However, these known devices are inaccurate and can have a non-negligible margin of error that is reflected in an erroneous characterization of the fiber.

In addition, the cotton fibers subjected to the measurement of the moisture content and those subjected to the measurement of the length or of the dynamometric characteristics, although drawn from a same sample, may have a different moisture content; the results of the measures carried out on them, therefore, may not be correlated to one another.

Devices are also known, which integrate the measurement of the moisture content, of the length and of the dynamometric characteristics of the cotton fibers, which devices are supplied as stand-alone apparatuses or as modules integrated in more complex apparatuses provided with a plurality of measuring modules, each of which is adapted to measure different characteristics of the cotton fibers.

These known devices are fed with a sample of cotton fibers that is compacted by pressing between two plates; the sample thus compacted is subjected to a measurement of the moisture content through resistive devices based on the measurement of its electrical conductivity.

After the measurement of the moisture content, a metal comb withdraws from the compacted sample a set of textile fibers, which are subsequently carded and brushed so as to be parallelized in order to form a line of textile fibers, substantially coplanar and parallel to one another, said line being called "beard" in the jargon of the industry. The metal comb is movable towards a measuring area at which are placed measuring means (e.g. of the optic or capacitive type) for measuring the length of the fibers forming the "beard" and dynamometer means for measuring the elongation and the tensile strength of the fibers forming the "beard".

However, these known devices as well have some drawbacks.

On one hand, as pointed out above, devices of the resistive type for measuring the moisture content are inaccurate and provide measurements with non-negligible errors.

On the other hand, it is evident that the moisture content of the "beard" of textile fibers withdrawn from the compacted sample and subsequently subjected to the measurements of the length and of the dynamometric characteristics can be even markedly different from the moisture content measured on the compacted sample from which that same "beard" was withdrawn. The temperature inside these devices, the handling of the fibers of the sample and of the "beard" withdrawn therefrom, the time that elapses between the measurement of the moisture content of the compacted sample and the measurement of the length and of the dynamometric characteristics of the fibers of the "beard" withdrawn therefrom are, in fact, factors that can change in a non-negligible manner the moisture content of the fibers.

Therefore, in this case too, the values of the length and of the dynamometric characteristics measured on the fibers of the "beard" withdrawn from a sample may not be correlable with the moisture content previously measured on that sample.

A purpose of the present invention is to overcome the drawbacks of the prior art.

Within this general object, a particular purpose of the present invention is to provide a measuring method and device for measuring the moisture content (i.e. the water content), the length and/or at least one dynamometric characteristic of textile fibers, in particular cotton fibers, which allows obtaining values of the moisture content, of the length and/or of the dynamometric characteristics that are accurate and that can be correlated to one another.

Another purpose of the present invention is to provide a measuring device for measuring the moisture content (i.e. the water content), the length and/or at least one dynamometric characteristic of textile fibers, in particular cotton fibers, that is functional and that can be used as a stand-alone apparatus or integrated as a module in a modular apparatus for measuring a plurality of characteristics of textile fibers.

According to the present invention, these and other purposes are achieved through a method for measuring the moisture content (i.e. the water content), the length and/or at least one dynamometric characteristic of textile fibers, in particular, cotton fibers, comprising the steps of:

a) pressing a layer of textile fibers between a pair of plates parallel to one another;
b) withdrawing a line of textile fibers, known in the jargon of the industry as "beard", from said layer thus pressed, and making the textile fibers of said line substantially coplanar and parallel to one another;
c) bringing the line of textile fibers to a measuring area at which at least to perform one measuring step selected from
d1) measuring the length of the textile fibers of said line of textile fibers, and
d2) measuring at least one dynamometric characteristic selected from the group comprising tensile strength and tensile elongation of the textile fibers of said line of textile fibers;
e) removing the textile fibers of said line of textile fibers from the measuring area after having performed the at least one measuring step d1) and d2); and
f) measuring the moisture content of the textile fibers forming said layer and/or forming said line of textile fibers by means of microwave sensors for measuring moisture, wherein:
   if step f) of measuring the moisture content of the textile fibers is carried out on the textile fibers forming said layer, it is carried out during or after step a) of pressing said layer and before step b) of withdrawing said line of textile fibers therefrom,
   if step f) of measuring the moisture content of the textile fibers is carried out on the textile fibers forming said line of textile fibers, it is carried out after step b) of withdrawing said line of textile fibers from said layer and in a step preceding or simultaneous with said step e) of removing the textile fibers of said line of textile fibers from said measuring area.

In any case, step f) of measuring the moisture content (i.e. the water content) of the textile fibers is carried out by means of microwave sensors for measuring the moisture and, as known, it comprises the steps of:

f1) generating a microwave field in a microwave resonator so as to produce a substantially homogeneous microwave field in a measurement volume,
f2) placing the fibers of said layer or of said line of textile fibers close to or into said measurement volume,
f3) detecting variations of the frequency and/or of the width of the resonance curve of said microwave field generated by the proximity or by the presence of said fibers of said layer or of said line of textile fibers in said measurement volume, and
f4) processing, with known functions or algorithms, the variations thus detected in order to generate a value of the moisture content of the textile fibers of said layer or of said line of textile fibers.

Microwave sensors for measuring moisture are known in themselves, e.g. those produced by the company TEWS ELEKTRONIK GmbH & Co. KG. Also known are the functions or the algorithms that allow processing the variations in the frequency and/or in the width of the resonance curve of the microwave field generated by the proximity or by the presence of textile fibers and detected with them in order to generate a value of the moisture content of these textile fibers, described for example in U.S. Pat. No. 5,397,993 to TEWS ELEKTRONIK, the content of which is herein referenced in its entirety. In particular, the values of the moisture content thus determined are independent of the density of the sample (tuft) of textile fibers.

The textile fibers are, in particular, cotton fibers.

In a preferred embodiment, the measuring step comprises, in succession one after the other, the step d1) of measuring the length of the textile fibers of the line of textile fibers and step d2) of measuring at least one dynamometric characteristic selected from the group comprising the tensile strength and the tensile elongation of the textile fibers of the line of textile fibers.

In a possible embodiment, step f) of measuring the moisture content of the textile fibers is carried out on the fibers forming said layer during or after the step a) of pressing the layer of textile fibers and before step b) of withdrawing a line of textile fibers ("beard") therefrom.

In a further possible embodiment, step f) of measuring the moisture content of the textile fibers is carried out on the textile fibers forming said line of textile fibers ("beard") after step b) of forming the line of textile fibers and before the at least one measuring step for measuring d1) their length or for measuring d2) at least one dynamometric characteristic thereof.

Advantageously, step f) of measuring the moisture content of the textile fibers is carried out on the textile fibers forming said line of textile fibers ("beard") after step b) of forming the line of textile fibers and during step c) wherein the line of textile fibers thus formed is brought to the measuring area and, still more advantageously, to the inlet of said line of textile fibers in said measuring area.

In a further possible and advantageous embodiment, step f) of measuring the moisture content of the textile fibers is carried out on the textile fibers forming said lines of textile fibers ("beard") at the measuring area before or after the at least one measuring step for measuring d1) their length or for measuring d2) at least one dynamometric characteristic thereof. If the textile fibers forming the line of textile fibers are subjected in succession to the step of measuring d1) their length and to the step of measuring d2) at least one dynamometric characteristic thereof, step f) of measuring their moisture content can take place before or after each of such two measuring steps d1) and d2).

In a further possible embodiment, step f) of measuring the moisture content of the textile fibers is carried out on the textile fibers forming said line of textile fibers after the at least one or both the measuring steps d1) and d2) and before or during step e) of removing them from the measuring area. In particular, if a step of measuring the dynamometric characteristics is provided, step f) of measuring the moisture content of the textile fibers is carried out immediately after this step of measuring the dynamometric characteristics and during their removal from the measuring area. Preferably, the removal takes place by suction of the textile fibers forming the lines of textile fibers from the measuring area, in this case the measurement volume is defined by a portion of the suction volume.

Step f) of measuring the moisture content of the textile fibers forming the layer and/or the line or "beard" can be carried out both on the fibers forming the layer, during or after step a) of pressing said layer, and on the fibers forming the line or "beard" after step b) of forming it in one or more of the moments described above.

Step f) of measuring the moisture content of the textile fibers forming the layer and/or the line or "beard" is advantageously carried out through the use of microwave sensors for measuring the moisture content of the type, for example, of those produced by the company TEWS ELEKTRONIK GmbH & Co. KG.

In general terms, such microwave sensors for measuring the moisture content comprise a body that defines a resonating cavity for microwaves, a microwave generator that is associated with that body to generate a microwave field in said resonating cavity and a detector of the resonance characteristics and of variations thereof. The generator and the detector are connected to an electronic processing and control unit, e.g. as described in U.S. Pat. No. 5,397,993.

Such microwave sensors for measuring the moisture content can be of the planar type, "forked", i.e. consisting of two half cylinders facing one another, between which a microwave field is generated, or of the tubular type. For example, microwave sensors of the planar type can be used for measuring the moisture content of the textile fibers forming the layer pressed between the pair of plates. Microwave sensors of the "forked" or double type can be used for measuring the moisture content of the fibers forming the line or "beard" after step b) of forming the line or "beard" and during step c) in which the line or "beard" is brought to the measuring area and/or before or after step d1) of measuring their length and before the possible step d2) of measuring their dynamometric characteristics. Or, microwave sensors of the tubular type can be used for measuring the moisture content of the fibers forming the line or "beard" during step e) of removing from the measuring area. Said removal generally takes place by suction of the textile fibers along an evacuation conduit, along a section of which it is possible to place a microwave sensor of the tubular type.

As it is easily comprehensible to the skilled person, a preliminary step of calibrating such microwave sensors is necessary in order to build, by interpolation of points obtained through experimental measurements, a calibration curve that correlates the values of the moisture content obtained through such microwave sensors with values of the moisture content expressed as percentages. This calibrating step is carried out by preparing a plurality of samples of textile fibers (cotton fibers) conditioned to different degrees of humidity and temperature in compliance with the current standards, subjecting the samples thus prepared to a measurement of the degree of moister through the selected microwave sensor and subjecting the same sample to a measurement of its "moisture regain value" in accordance with the current standards. The two measurements carried out on each sample are correlated to form a calibration point; the calibration points obtained experimentally are then interpolated to originate a calibration curve.

Step b) of forming the line or "beard" of fibers takes place, in a known manner, by withdrawing tufts of fibers from the pressed layer by means of a metal comb co-operating with a jaw element, by carding the tufts of fibers thus withdrawn to eliminate therefrom excesses or fibers not well anchored and by brushing the fibers to make them parallel to one another.

Steps d1) and d2) of measuring the length of the fibers and their dynamometric characteristics are advantageously carried out, in succession one after the other, in a same measuring area whereinto the line or "beard" of fibers is introduced by means of the same metal comb.

Step d1) of measuring the length comprises, in a known manner, the detection of variations of electro-optical fields crossed by the line or "beard" of fibers.

Step d2) of measuring the dynamometric characteristics of the fibers forming the line or "beard" comprises, in a known manner, gripping through a pair of pliers, one of which is made relatively movable with respect to the other, two end portions of the fibers and subjecting the fibers thus clamped at the opposite ends to a pulling action moving the movable pliers away from the fixed pliers. The detection of the relative displacement of the movable pliers with respect to the fixed pliers and of the force applied to the fibers allows determining the tensile elongation (i.e. the elongation subjected by the fibers before breaking) and the tensile strength (i.e. the maximum stress applied to the fibers before breaking) of the fibers.

At the end of the measuring step d1) and/or d2) the fibers are released and removed from the measuring area preferably by suction.

The measurement of the moisture content of the fibers forming the line or "beard", after the latter has been formed, in times (in the order of less than 5-10 seconds) and locations close to those for measuring their length and/or their dynamometric characteristics allows correlating the values of the moisture content to the values of the dynamometric characteristics with a reduced margin of error.

The measurement of the moisture content of the fibers forming the pressed layer from which the line or "beard" is withdrawn and/or forming the line or "beard" itself by detecting variations of the frequency and of the amplitude of the resonance curve of a microwave field crossed or anyway applied to these fibers is accurate and reliable; in fact, it provides values with small errors. Moreover, said measurement is independent of the degree of uniformity of the distribution of water (moisture) in the fibers and of the density of the tuft of fibers.

The present invention also relates to a measuring device for measuring the moisture content, the length and/or at least one dynamometric characteristic of textile fibers, in particular, cotton fibers, as outlined in independent claim 6 and additional characteristics of which are specified in the dependent claims.

The characteristics and advantages of a measuring device for measuring the moisture content, the length and/or at least one dynamometric characteristic of textile fibers, in particular, cotton fibers, according to the present invention will become more apparent from the following exemplary and non-limiting description, referred to the enclosed schematic drawings in which:

FIGS. 10A to 10C are axonometric views of a further module of the apparatus of FIGS. 1 and 2 comprising a measuring device for measuring the fineness and maturity of the textile fibers, in particular cotton fibers, in successive operating positions;

Figure 1:
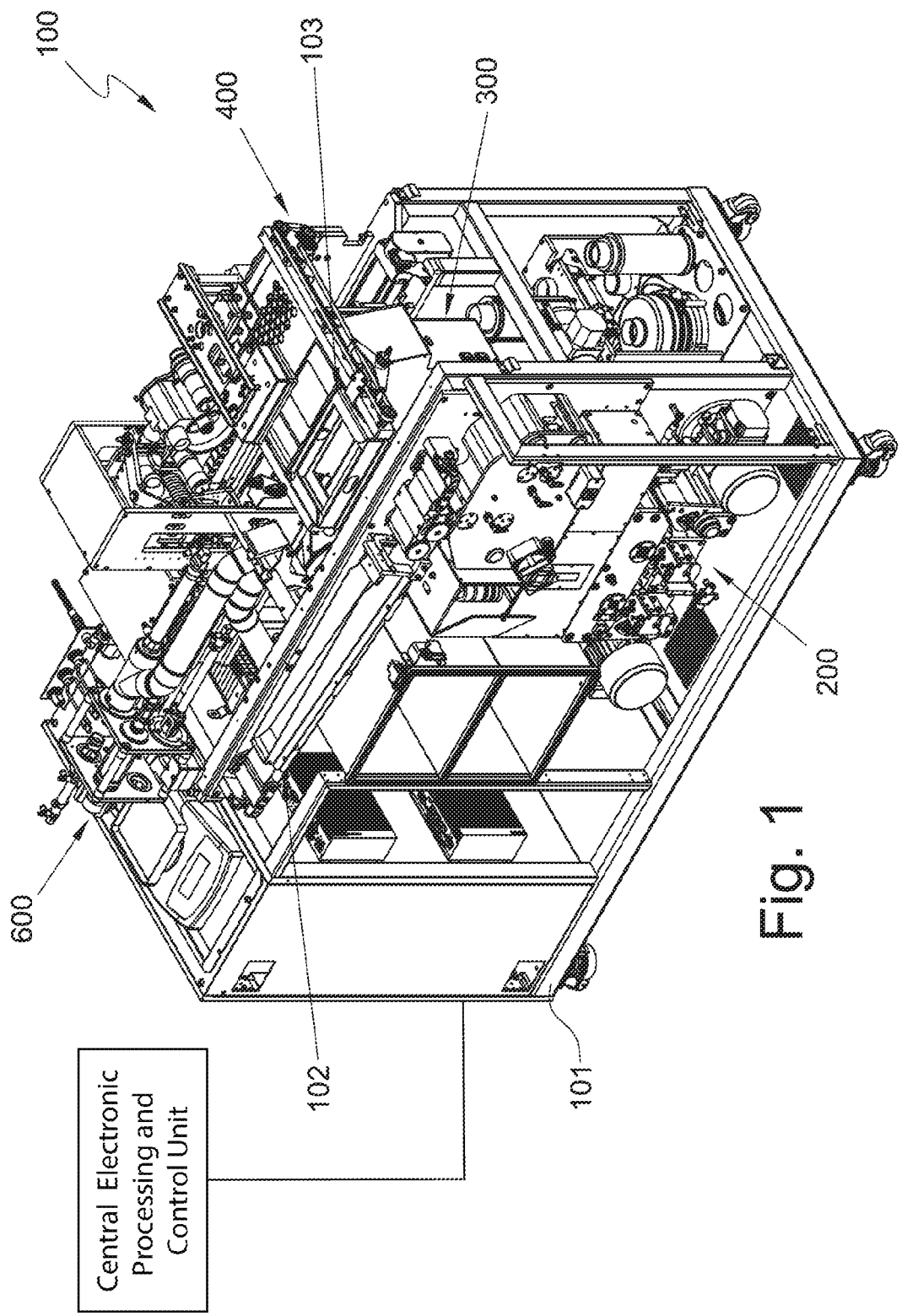
FIGS. 1 and 2 are axonometric views of a modular apparatus for measuring characteristics of cotton fibers, wherein one of the measuring modules consists of the measuring device according to the present invention.

With reference to the figures, the reference number 100 entirely indicates a modular apparatus for measuring a plurality of characteristics of textile fibers, in particular cotton fibers.

For the sake of simplicity, hereinafter reference will be made to fibers, by meaning textile fibers and in particular textile fibers of a vegetable nature and even more in particular cotton fibers.

The apparatus 100 comprises a support structure 101 that supports a plurality of modules each comprising at least one measuring device for measuring at least one characteristic of the textile fibers and a central electronic processing and control unit for controlling said modules, which is not shown being of the type known to the skilled person. It is noted that each module constituting the apparatus 100 can be provided with an own local electronic processing and control unit, in turn connected to the central electronic processing and control unit.

In the embodiment shown in the enclosed figures, the apparatus 100 comprises:
- a first module comprising a measuring device 200 for measuring the cotton stickiness and the imperfections, such as neps, and/or impurities, such as seeds fragments, residues of insects or artificial fibers, in particular polymeric fibers or others, present in the cotton fibers.
- a second module comprising a measuring device 300 for measuring the color and for detecting impurities of the cotton fibers,
- a third module comprising a measuring device 400 according to the present invention for measuring the moisture content, the length and/or at least one dynamometric characteristic selected from the group comprising tensile elongation (i.e. the elongation undergone by the fibers before breaking) and the tensile strength (i.e. the maximum stress applied to the fibers before breaking),
- a fourth module comprising a device 600 for measuring the fineness and of the maturity of the cotton fibers.

The apparatus 100 is provided with two devices for the inlet of a respective sample of fibers to be tested:
- a first inlet device 102, of the conveyor belt type, for inletting a first sample, which feeds the measuring device 200 for measuring the stickiness and the imperfections and/or impurities, and
- a second inlet device 103, of the movable drawer type, for inletting a second sample and which feeds in succession the measuring device 300 for measuring the color and detecting impurities and the measuring device 400 for measuring the moisture content (i.e. water content), the length and/or the dynamometric characteristics of the fibers.

The measuring device 600 for measuring the fineness and maturity of the fibers is fed by a pneumatic system that withdraws the fibers exiting from the measuring device 200 for measuring the stickiness, the imperfections and/or the impurities and conveys them into the measuring device 600.

The measuring device 400 for measuring the moisture content, the length and/or the dynamometric characteristics of the fibers according to the present invention is placed in succession to the measuring device 300 for measuring the color and detecting impurities of the fibers forming a same sample fed by the second inlet device 103.

The second inlet device 103 is of the type of a drawer 104 that is filled with fibers and is movably guided along a path that crosses the measuring device 300 and that introduces the sample into the measuring device 400.

The drawer 104 consists of a frame; the opposite faces of the drawer 104 that are parallel to the sliding plane of the drawer itself are open.

The measuring device 300 comprises, in a known manner, a board 301 whereon the drawer 104 is made to slide.

The board 301 comprises a plate 302 of a material transparent to light, below which a compartment 303 is obtained, which contains devices for optically analyzing the fibers of the sample contained in the drawer 104. Such optical analysis devices comprise, for example, a TV camera 304 advantageously in color and/or a spectrophotometer 305 and allow recognizing the hue degree of the fibers and the presence of impurities therein, e.g. residues of insects and/or vegetables (such as seed fragments).

The measuring device 400 according to the present invention is positioned in succession to the measuring device 300, and said two devices can be integrated in a unique module.

The measuring device 400 comprises a housing 401 that is integrated in the support structure 101 and in which two areas are defined:
- a preparation area ZP of a line or "beard" of fibers that are arranged substantially parallel and coplanar to one another and
- a measuring area ZM in which the fibers forming the line or "bear" are subjected to the measurements of length and/or of the dynamometric characteristics and advantageously to both of these measurements in succession.

Figure 4:
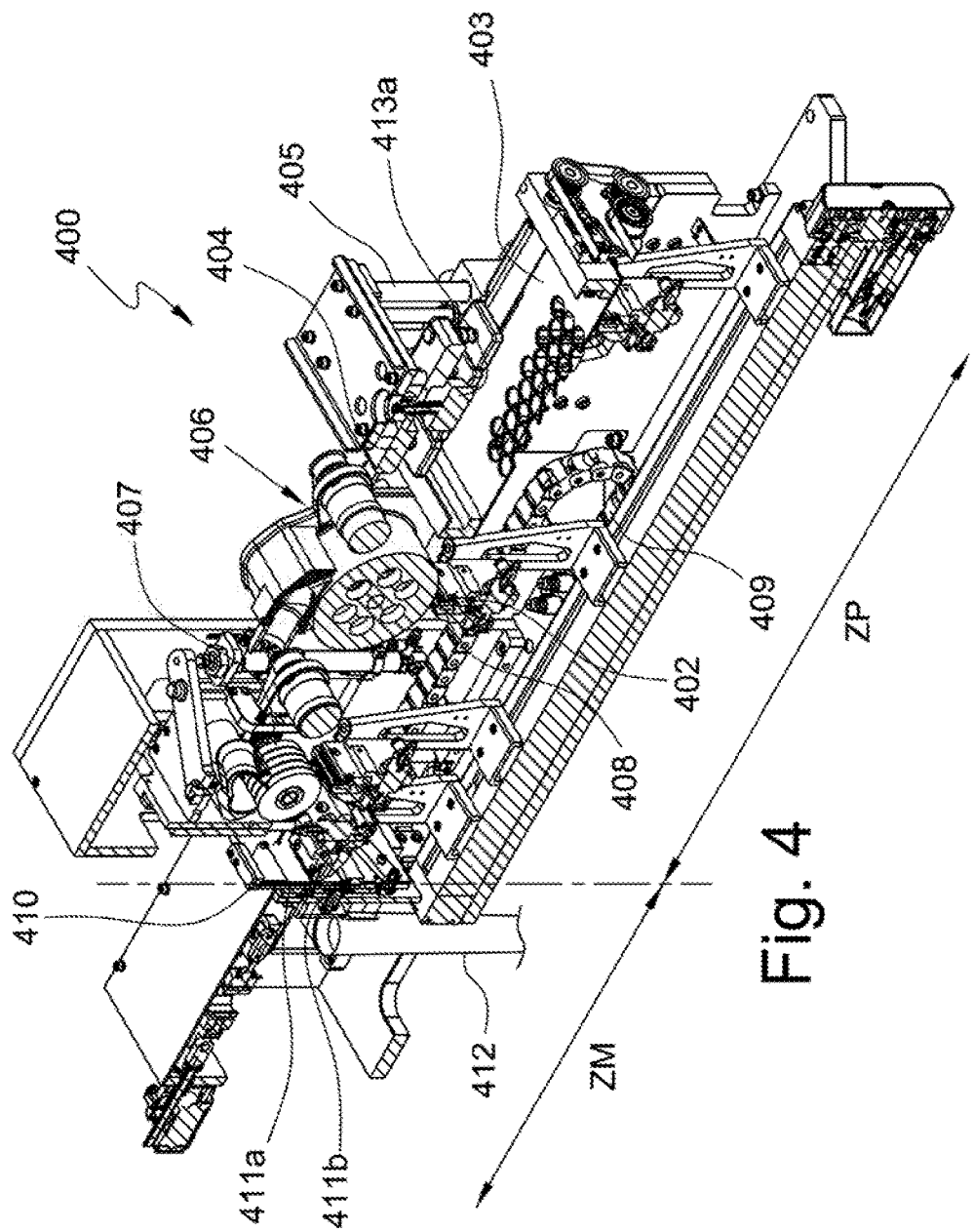
FIG. 4 is a schematic section view of the module of FIG. 3 with the comb for drawing the line of textile fibers in different operating positions.

The line or "beard" of fibers is handled and carried between the preparation area ZP and the measuring area ZM by a metal comb 402 that is associated with the housing 401 in movable manner with the possibility of effecting both translation and rotation movements, schematically shown in FIG. 4.

The preparation area ZP comprises:
- a grid or anyway a perforated plate 403 positioned along the sliding path of the drawer 104 in succession to the board 301 and coplanar thereto;
- a pressure plate 404 that is positioned above the perforated plate 403 and that is substantially parallel thereto and that is supported in movable manner towards and away from the perforated plate 403 along a directional that is orthogonal thereto, linear actuator means 405 for the sliding of the pressure plate 404, card means 406, brush means 407 and suction means positioned in succession alongside the "press" formed by the perforated plate 403 and by the pressure plate 404.

Advantageously, the linear actuator means 405 are of the pneumatic cylinder-piston type and comprise a proportional pressure regulator configured and controlled to keep the pressure of the operating fluid substantially equal to a pre-set value, in order to ensure that the layer of sample interposed between the pressure plate 404 and the perforated plate 403 is pressed under pre-set known conditions.

The comb 402 is coupled with a jaw element 408 that is movable between a closed position and an open position. The comb 402 with the jaw element 408 coupled thereto is supported by a head mounted on a bracket; the bracket is movable to slide along a rectilinear guide 409 and is actuated along said rectilinear guide 409 by a linear actuator (of the type, for example, with a motor-driven ball screw-nut screw coupling), by means of which, and with it the comb 402 and the jaw element 408, it is actuated along the preparation area ZP and towards the measuring area ZM. The head that supports the comb 402 and the jaw element 408 coupled thereto can then rotate about a horizontal axis (parallel to the perforated plate 403) orthogonal to the sliding direction defined by the rectilinear guide 409.

The comb 402 is adapted to hook the fibers forming a line or "beard".

In a known manner, the drawer 104 is made to slide so as to be positioned above the perforated plate 403. The pressure plate 404 is approached to the perforated plate 403 and pressed thereon by the actuator means 405, the sample of fibers interposed between the two plates forms a pressed layer that forms protuberances that project from the openings of the perforated plate 403 at the lower face thereof (i.e. of the face of the plate 403 opposite the one facing the pressure plate 404).

Advantageously, the proportional pressure regulator allows applying to the layer of fibers a constant pressure equal to a pre-set value; on the value of this pressure depends the degree of compaction of the pressed layer and the size of its protuberances projecting from the perforated plate 403.

The comb 402 is brought below the perforated plate 403 in order to withdraw a line of fibers from the protuberances formed by the layer pressed against the perforated plate 403 itself.

The comb 402 is then translated in succession first at the card 406 that eliminates the excess fibers from the line or "beard" and then at the brush 407 that parallelizes the fibers of the line or "beard". During these steps the comb 402 is arranged with the tines horizontal and the jaw element is in the open position. The line or "beard" of fibers thus parallelized and substantially coplanar is tightened on the comb 402 by the jaw element 408, rotated in the horizontal position and brought at the inlet of the measuring area ZM.

In the measuring area ZM the following are located:

measuring means 410 for measuring the length of the fibers forming the line or "beard", dynamometer means for measuring at least one dynamometric characteristic and that comprise pliers members that comprise fixed pliers 411a and movable pliers 411b, the latter moving towards and away from the fixed pliers 411a, the fixed pliers 411a and the movable pliers 411b clamping two end portions of the line or "beard" of fibers, detection means (not described in detail, being of the known type) for detecting the relative displacement of the movable pliers 411b with respect to the fixed pliers 411a when both the movable and the fixed pliers are in the gripping and holding position of respective portions of the fibers of the line or "beard", detection means (not described in detail, being of a known type) for detecting the tensile force applied to the fibers of the line or "beard" during the relative movement of the movable pliers 411b with respect to the fixed pliers 411a when both the movable and the fixed pliers are in the gripping and holding position of a respective portion of the fibers forming the line or "beard".

In addition, extraction means 412 are provided for extracting the textile fibers of the line or "beard" from the measuring area ZM. These extraction means 412 comprise a conduit that has one end in communication with the measuring area ZM and the opposite end associated with suction means adapted to create a vacuum of such extent as to retrieve the fibers and the segments thereof released by the pliers members at the end of the execution of the dynamometric tests.

The data pertaining to the relative displacement of the movable pliers 411b with respect to the fixed pliers 411a and to the tensile force applied by the movable pliers 411 to the fibers of the line or "beard" are then processed in a known manner to obtain dynamometric characteristics of the fibers themselves.

The possibility that the comb 402 may constitute the fixed pliers is not excluded.

According to a characteristic of the present invention, the measuring device 400 comprises measuring means 413 of the microwave type and comprising a microwave sensor for measuring the moisture content (i.e. water content) of the fibers forming the layer of fibers pressed between the pressure plate 404 and the perforated plate 403 and/or of the fibers forming the line or "beard", which measuring means 413 are placed respectively at the preparation area ZP and/or at the measuring area ZM and/or are associated with the extraction means 412 to detect the moisture content of the fibers forming the pressed layer and/or the line or "beard" just before and/or just after the execution of the measurement of their length and/or of the measurement of their dynamometric characteristics.

In a preferred embodiment the means 413 for measuring the moisture content are located at the inlet of the measuring area ZM or at the extraction means 412 to detect the moisture content of the fibers forming the line or "beard" already formed just before and/or just after the execution of the measurement of their length and/or of the measurement of their dynamometric characteristics. This allows measuring the moisture content of the same fibers that are subjected to the measurements of length and of the dynamometric characteristics, in times that are close to the execution of said measurements and substantially under the same environmental conditions in which said measurements are carried out. The values of length, of the dynamometric characteristics and of the moisture content can then be mutually correlated with good margins of certainty.

The means 413 for measuring the moisture content, as indicated above, are of the microwave type and comprise one or more microwave sensors for measuring the moisture content.

The use of microwave sensors for measuring the moisture content allows obtaining accurate measurements, with errors that are negligible and independent of the degree of distribution of water (moisture) in the fibers, as well as of the density of the sample (tuft) of fibers.

Sensors of this kind consist for example of the microwave sensors of the company TEWS ELEKTRONIK GmbH & Co. KG as described, e.g., in U.S. Pat. No. 5,397,993, the content of which is entirely referenced herein.

Such microwave sensors can be of the planar type, "forked", i.e. consisting of two half cylinders facing one another, between which a microwave field, or of the tubular type, is generated.

Figure 5A:
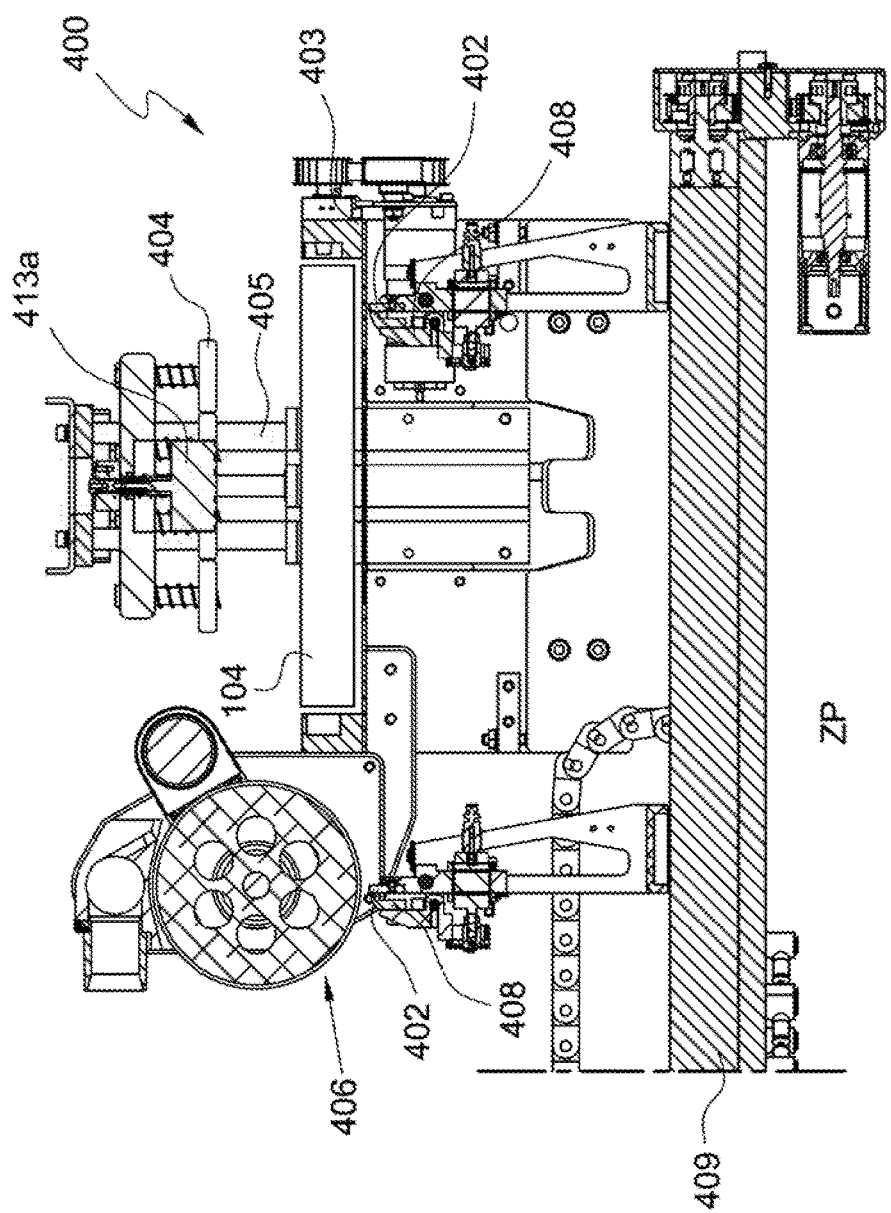
FIGS. 5A and 5B are enlarged scale views of two details of FIG. 4.
Figure 5B:
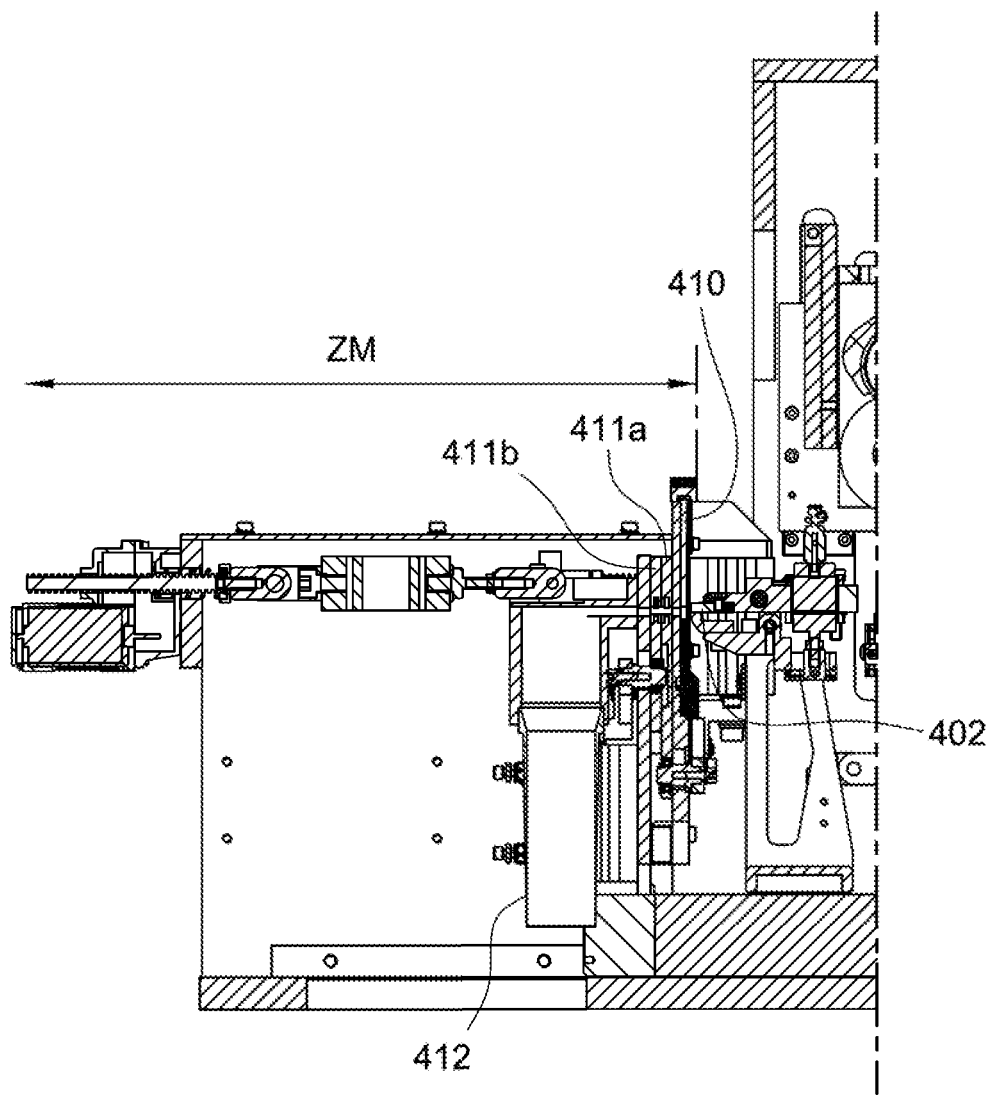

For example, in a possible embodiment shown in FIGS. 4 and 5A, the means 413 for measuring the moisture content are located at the preparation area ZP and comprise a microwave sensor 413A of the planar type supported by the pressure plate 404. The microwave sensor 413A is brought into contact with the layer of fibers pressed between the pressure plate 404 and the perforated plate 403 to detect the moisture content of the fibers forming the layer.

Figure 6:
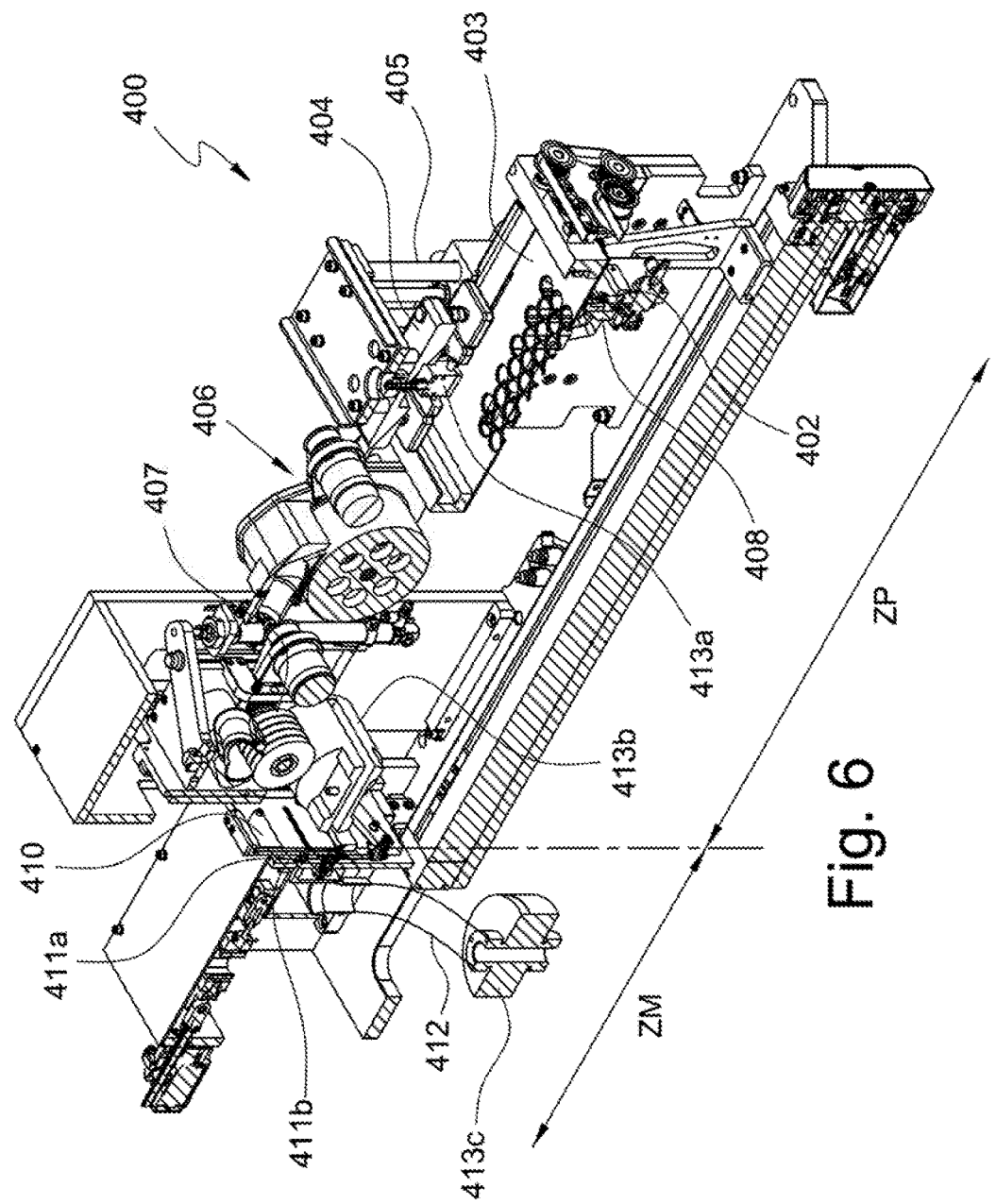
FIG. 6 is a schematic section view of the module of FIG. 3 that shows different possible configurations and arrangements of a microwave sensor.
Figure 7:
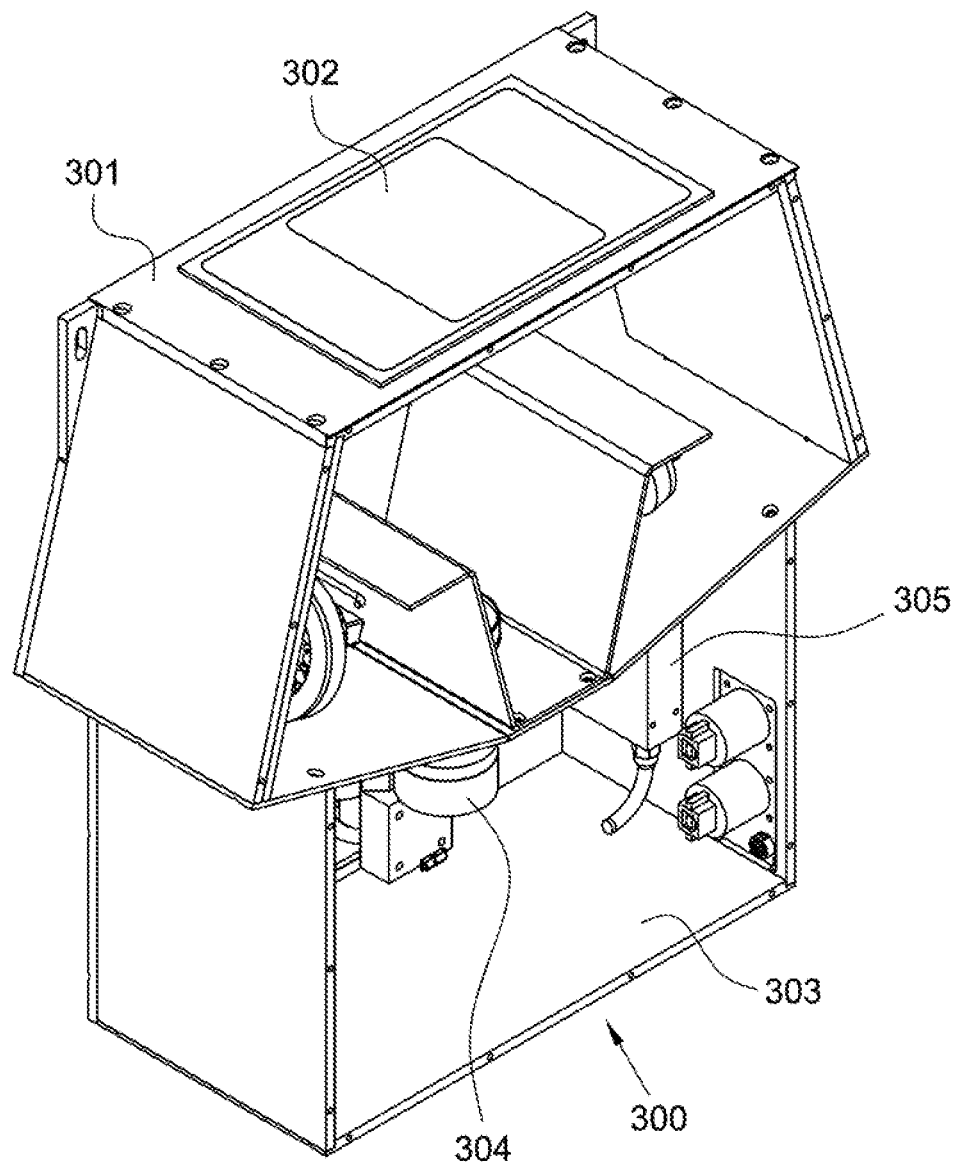
FIG. 7 is a schematic axonometric view of a further module of the apparatus of FIGS. 1 and 2 consisting of a measuring device for measuring the color and detection of impurities of the textile fibers.
Figure 8:
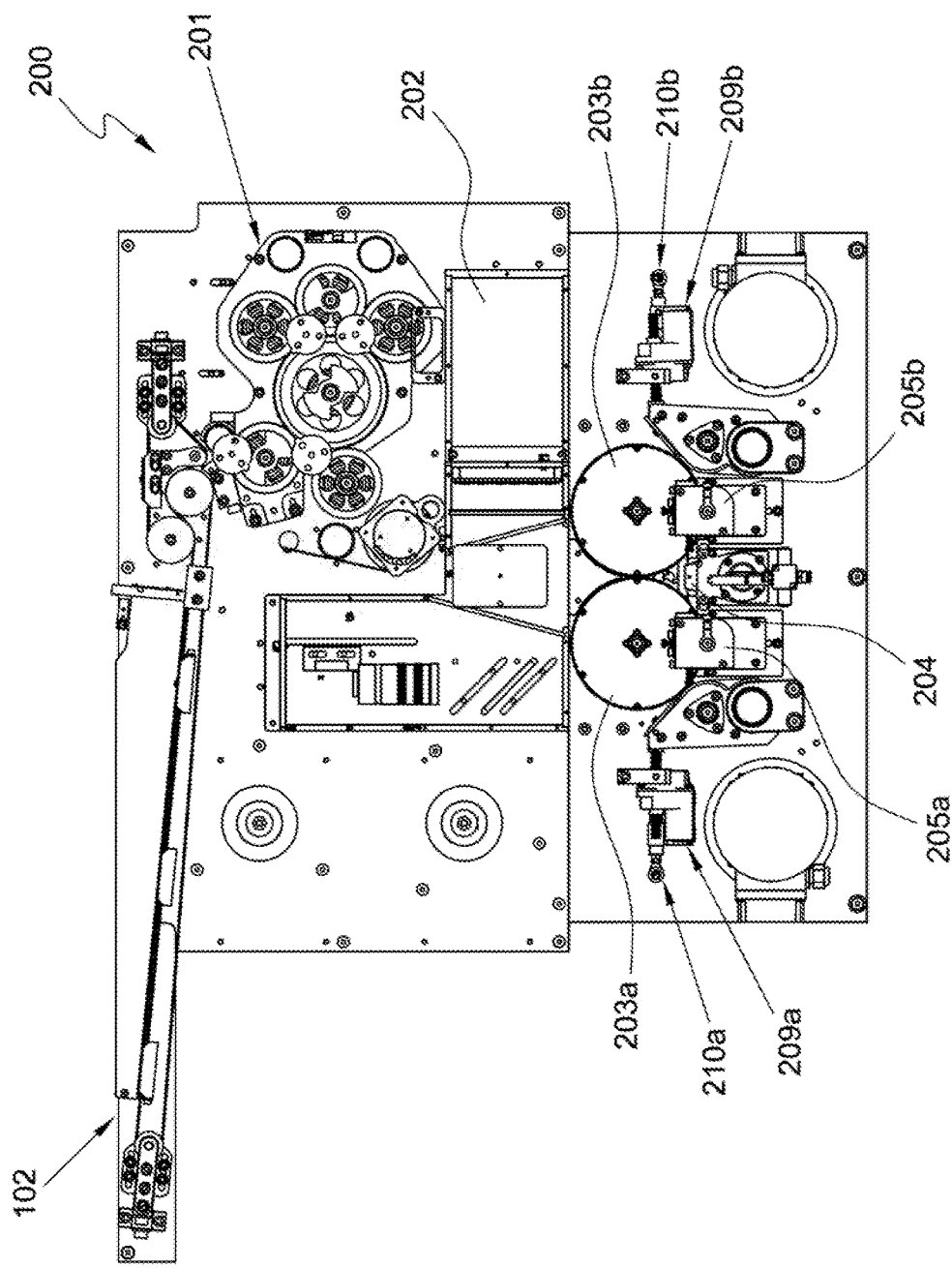
FIG. 8 is a schematic front view of a further module of the apparatus of FIGS. 1 and 2 consisting of a measuring device for measuring the stickiness and impurities and/or imperfections of the cotton fibers.
Figure 9:
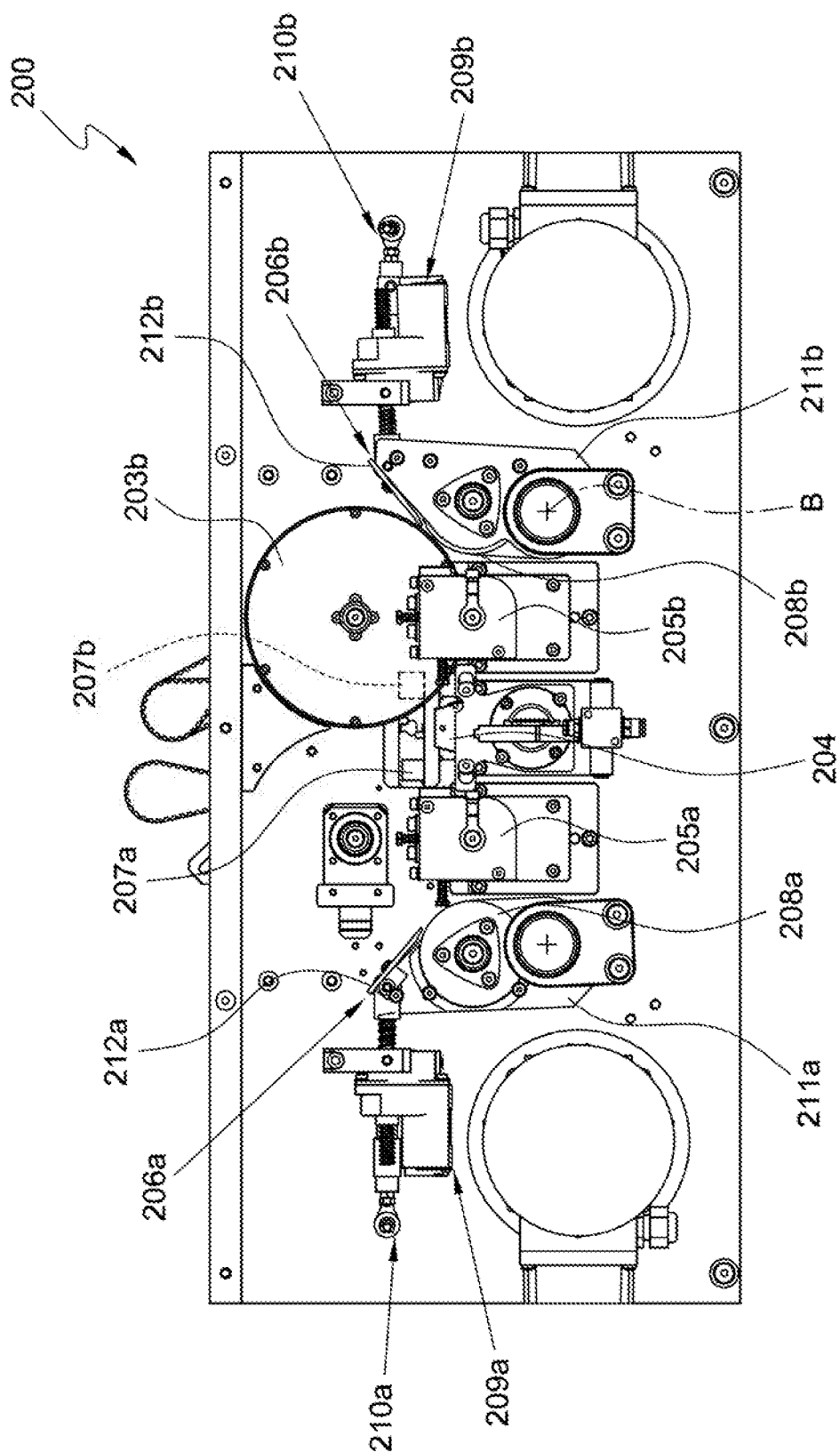
FIG. 9 is a schematic view of a detail of FIG. 8 with some parts removed.
Figure 10C:
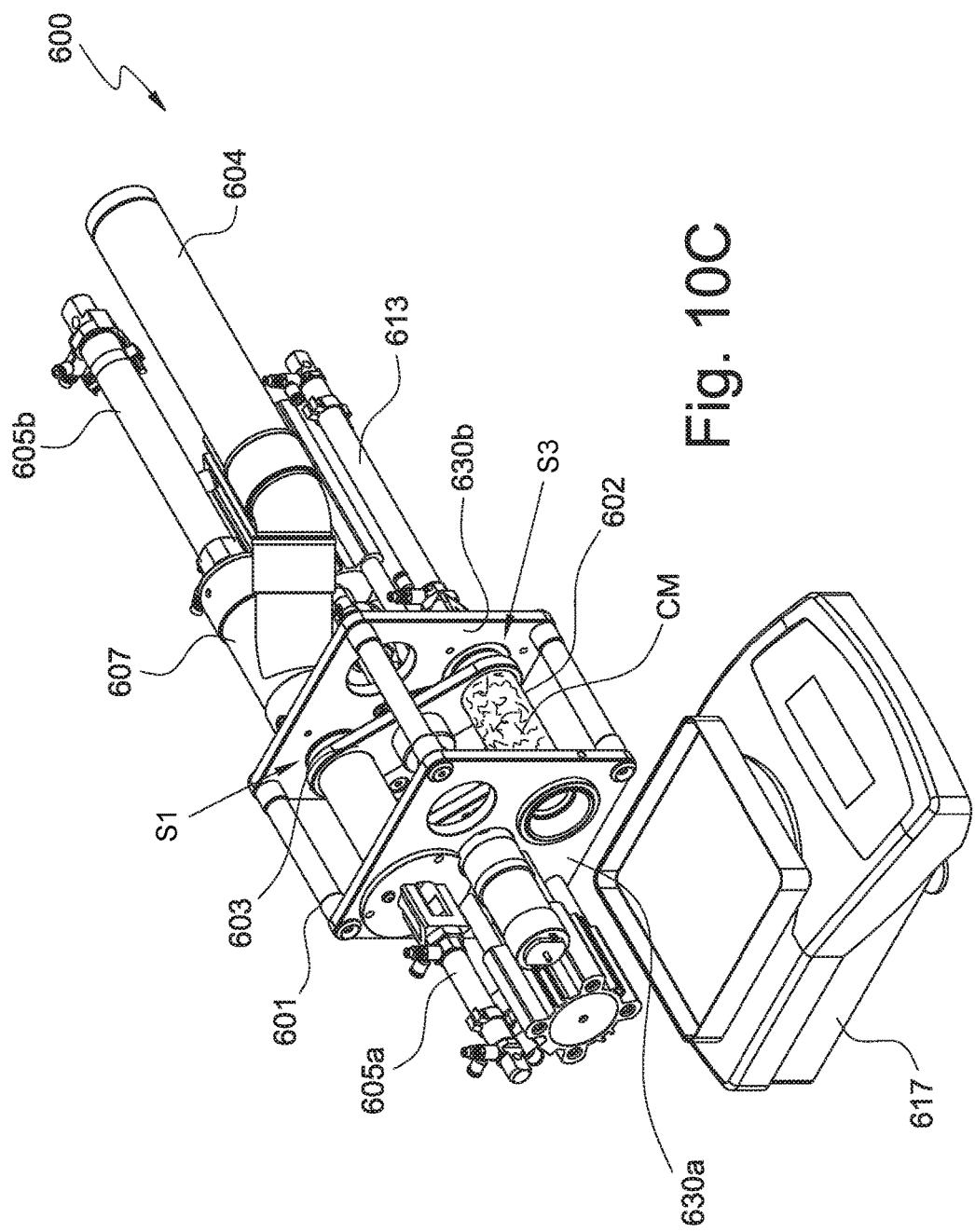
Figure 11:
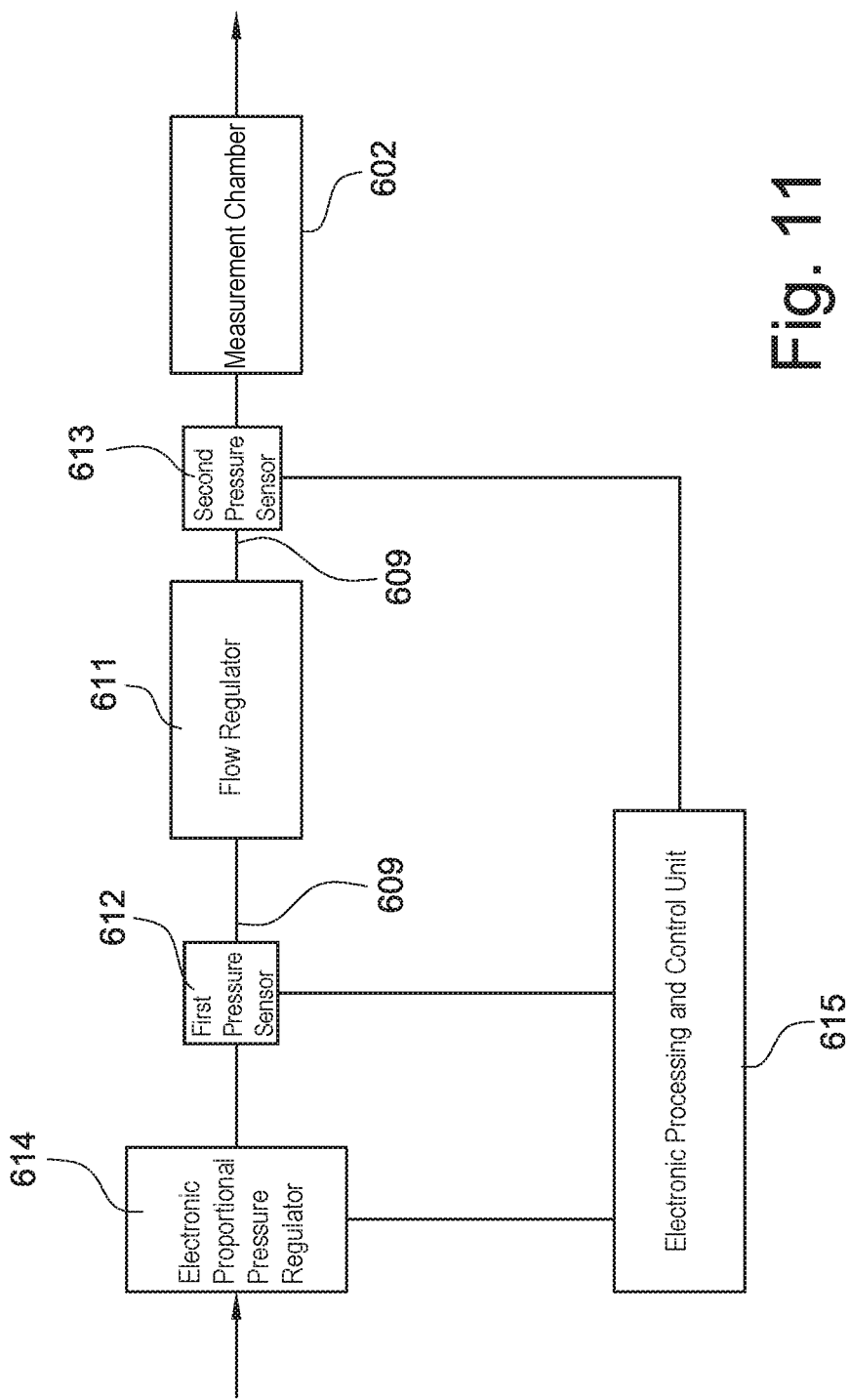
FIG. 11 is a diagram of the system for controlling the measuring device for measuring the fineness and maturity of the cotton fibers.

Alternatively or additionally, the means 413 for measuring the moisture content of the fibers comprise a microwave sensor 413B of the "fork" or double type for measuring the moisture content of the fibers forming the line or "beard" before measuring their length or after measuring their length and before measuring their dynamometric characteristics. With reference to FIG. 6, such a "fork" microwave sensor 413B is located at the inlet of the measuring area ZM.

Alternatively or additionally, the means 413 for measuring the moisture content of the fibers comprise a microwave sensor 413C of the tubular type positioned along the conduit of the extracting means 412.

In this latter case, the moisture content is measured on the fibers or on the segments of fibers released by the pliers members after the execution of the dynamometric tests and along the path away from the measuring area ZM.

Figure 2:
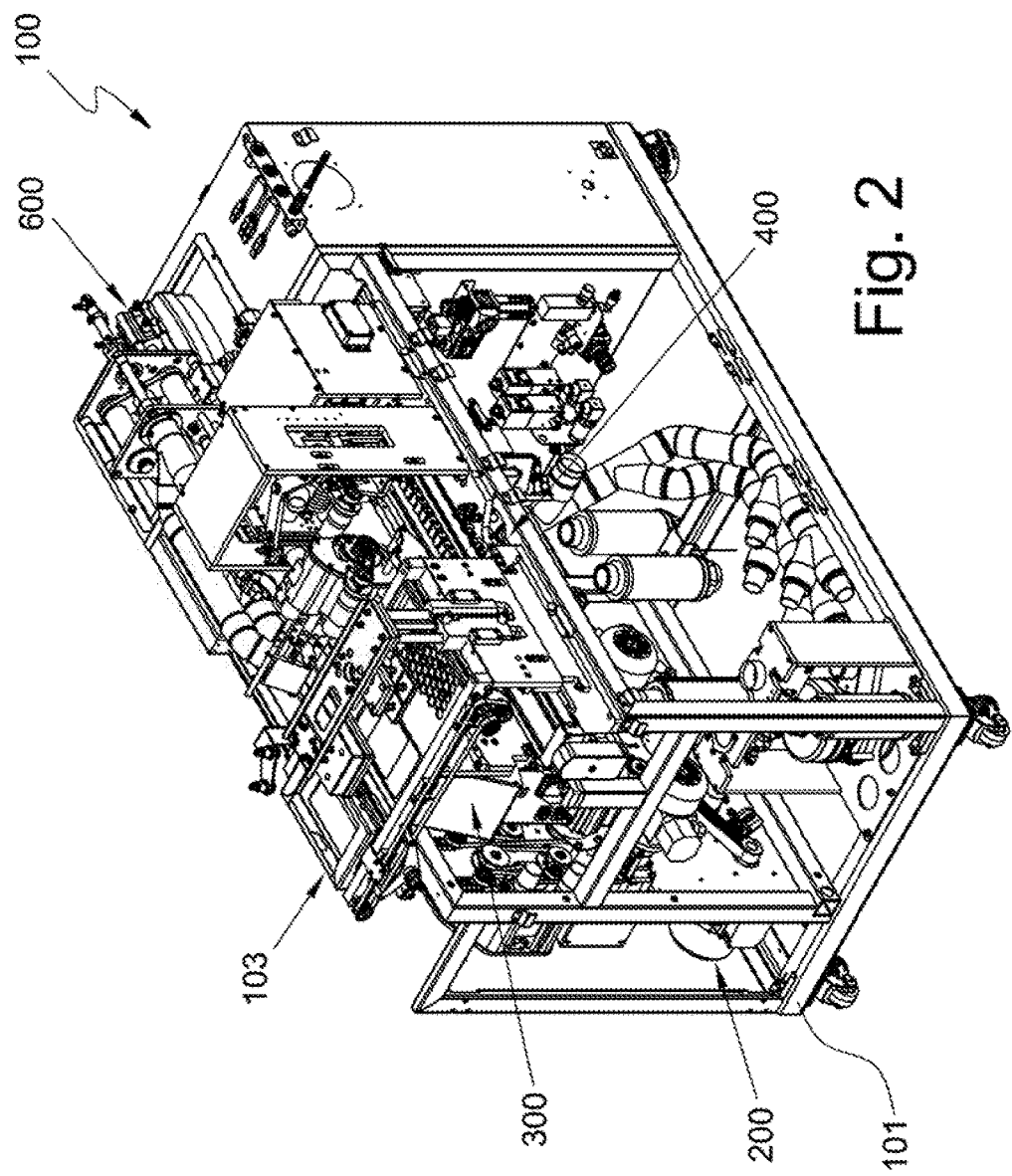
Figure 3:
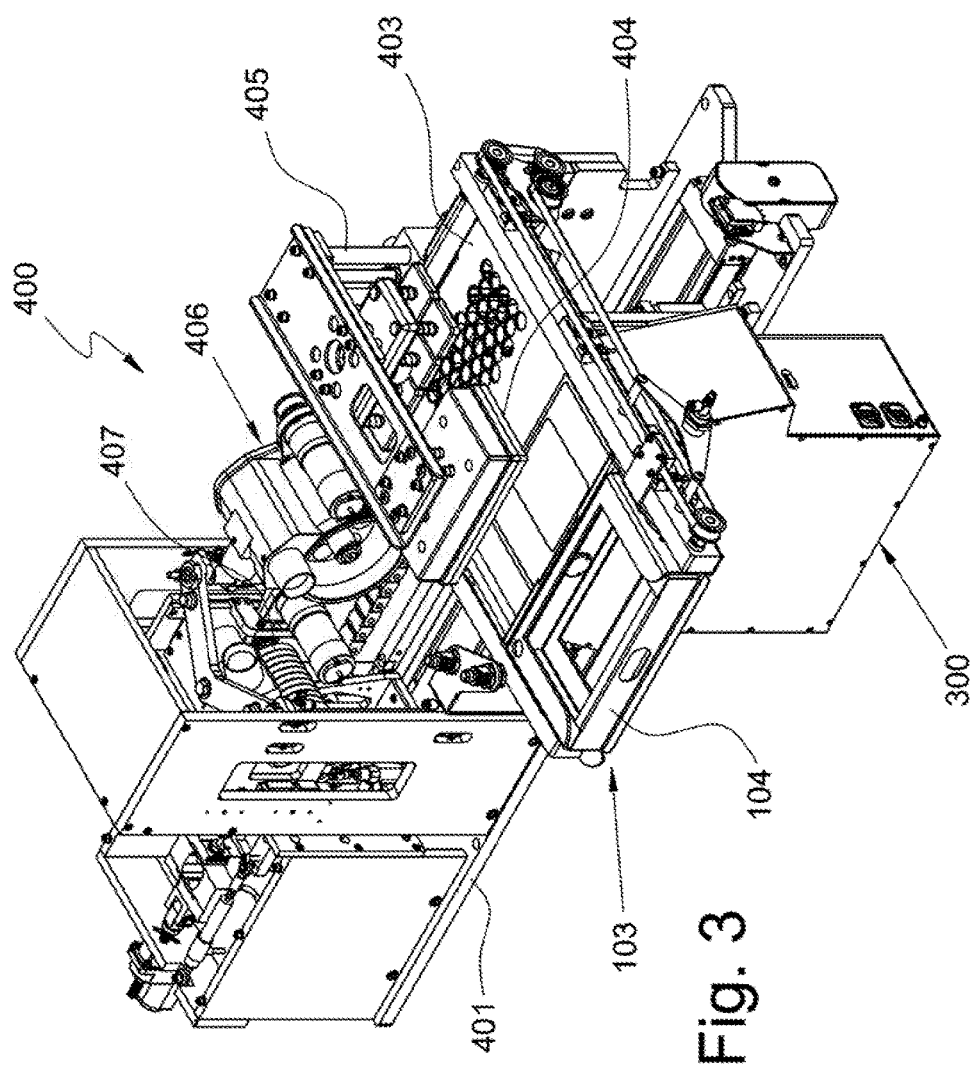
FIG. 3 is an axonometric view of the module of the apparatus of FIGS. 1 and 2 consisting of the measuring device according to the present invention.

For the sake of completeness, a description will be made of the remaining measuring devices forming the remaining modules of the apparatus 100, some of which are subject-matter of a separate patent application to the same Applicant. In any case, it is hereby specified that each of said measuring devices can be made as a stand-alone apparatus or integrated with one or more of the other measuring devices in a modular apparatus of the type of the apparatus 100 shown in FIGS. 1 and 2.

The measuring device 200 for measuring the stickiness and the imperfections and/or impurities of the fibers is, in general terms, of the type described U.S. Pat. No. 5,752,294.

The measuring device 200 is fed with a mass of fibers by the first inlet device 102 and comprises, arranged in mutual succession:
 card means 201 that receive at their inlet the mass of fibers fed by the first inlet device 102 and that are adapted to prepare and form a veil of fibers in a known manner,
 acquisition means 202 for acquiring images of the veil exiting from the card means 201,
 a pair of rollers 203a, 203b side by side to one another and counter-rotating and configured for measuring the stickiness,
 means 204 for dragging the veil advancing along the path defined by the card means 201, by the acquisition means 202 and by the pair of rollers 203a, 203b.

The card means comprise a plurality of cards that are not described in detail, being of the known type to the skilled person.

The acquisition means 202 comprise a compartment inside which are placed, for example, a TV camera advantageously in color or another optical sensor, one or more contrasting screens and/or devices for lighting one or both faces of the veil. The acquisition means 202 are connected to processing means configured to detect the presence of imperfections and/or impurities and possibly the shape and color of said imperfections and/or impurities. Advantageously, the TV camera is of the color type and it operates in combination with a first lighting group and/or with a second lighting group for lighting the veil, which face one another. This allows detecting and determining the type of the impurities present, be they vegetable fragments (grass or seed shells), of insects or of artificial fibers, such as polymeric fibers (polyethylene) deriving from bags and strings.

In this case as well the acquisition means 202 are not described further, being of a type immediately comprehensible to the skilled person.

Each roller 203a, 203b is associated with:
 heating means adapted to heat at least its outer lateral surface that contacts the veil in order to promote the adhesion of the sticky fractions of the fibers thereto,
 detecting means 205a, 205b for detecting the sticky fractions of the veil adhering thereto following the passage of the veil, and
 removing means 206a, 206b for removing the sticky fractions therefrom.

The measuring device 200 is also provided with an electronic processing and control unit that is not shown in the enclosed figures, being of the known type to the skilled person. Said electronic processing and control unit is advantageously of the programmable type and is connected or in any case integrated to the central electronic processing and control unit of the apparatus 100.

The operation of the heating means is controlled by the electronic processing and control unit according to the temperature of the rollers 203a, 203b detected by temperature sensor means 207a, 207b associated therewith. In greater detail, the heating means comprise for each roller 203a:
 at least one contact body 208a, 208b that is movably driven towards and away from the outer lateral surface of the respective roller 203a, 203b to exercise thereonto a friction action such as to develop heat, and
 actuator means 209a, 209b to actuate the displacement of said contact body 208a, 208b towards and away from the respective roller 203a, 203b,
wherein the electronic processing and control unit is adapted to control the actuator means 209a, 209b according to the signals emitted by the temperature sensor means 207a, 207b to vary the position of the respective contact body 208a, 208b with respect to the corresponding roller 203a, 203b.

Advantageously, moreover, position sensor means 210a, 210b are provided for detecting the position of the actuator means 209, 209b, which are connected to the electronic processing and control unit, wherein the electronic processing and control unit is adapted to control and command the actuator means 209a, 209b according to the signals emitted by the temperature sensor means 207a, 207b and by the position sensor means 210a, 210b.

Each contact body 208a, 208b consists of a brush roller that is rotatably supported by a support bracket 211a, 211b.

Each support bracket 211a, 211b has a first portion that is coupled to the housing 101 or in any case to the housing of the measuring device 200 rotatably about an axis B parallel to the axis of the respective brush roller and a second portion that is articulated to the actuator means 209a, 209b. The actuator means 209a, 209b are preferably of the linear type and, in the embodiment shown, comprise a screw-nut screw pair, the screw-nut of which is set in rotation by an electric motor and the screw of which has an end articulated to the respective support bracket 211a, 211b.

The position sensor means 210a, 210b consist of linear transducers associated with the screw of the respective actuator means 209a, 209b.

Each contact body 208a, 208b formed by a brush roller is actuated in rotation by respective own motor means controlled by the electronic processing and control unit. Depending on the signals emitted by the temperature sensor means 207a, 207b and by the position sensor means 210a, 210b, the electronic processing and control unit controls the actuator means 209a, 209b to modify the position of the contact bodies 208a, 208b with respect to the rollers 203a, 203b so as to modify the friction action exercised by the former onto the outer lateral surface of the latter and, consequently, the temperature reached by said surface in order to keep it close to a pre-set value (generally of approximately 38-40° C.) and suitable so that the sticky fractions of the veil that passes between the rollers 203a, 203b remain adhering to said surface.

It is thus possible to reach and keep the temperature of the rollers 203a, 203b at a pre-set value without possibility of errors, thus reducing the times of possible transitions.

Advantageously, moreover, at least one of the two rollers 203a, 203b is supported movably towards and away from the other along a direction that is orthogonal to their longitudinal axes and is coupled to means for actuating such a displacement. Pressure sensors are also provided, configured to detect, directly or indirectly, the contact pressure between the two rollers 203a, 203b. These sensors are, for example, force sensors configured to detect the force exerted by the actuator means acting on the movable roller or to detect the load acting on the support shafts of the two rollers. The electronic processing and control unit, be it local or central, is configured to control the means for actuating the mutual displacement of the two rollers according to the signals detected by the pressure sensors in order to keep the contact pressure between the two rollers substantially constant and close to a pre-set value. In fact, the degree of stickiness, as known, also depends on the pressure that the two counter-rotating rollers exert on the veil of fibers.

The sensor means 205a, 205b are of the laser type and are not further described, being of the known type to the skilled person. The signals detected thereby are sent to and processed by the electronic processing and control unit.

The removing means 206a, 206b consist of the same contact bodies 208a, 208b in the form of brush rollers and rotating and higher angular velocities than those of the respective rollers 203a, 203b and of a spatula or blade 212a and 212b. In this case as well the removing means 206a, 206b are not further described, being of the known type to the skilled person and being able to have different embodiments.

The dragging means 204 are of the suction (vacuum) type and are configured to exercise a sufficient action on the veil to allow its advancement along the path downstream of the card means 201 and along the image acquisition means 202 and the pair of rollers 203a, 203b anyway without preventing the adhesion of the sticky fractions to the rollers 203a, 203b.

With reference to FIGS. 10A-10C and 11 the measuring device 600 for measuring the fineness and the maturity of the cotton fibers will be herein described, which operates according to known flow rate measurement methods.

As known, mature cotton fibers have hollow cross-section and appear as a flattened fluff, the inside of which consists of a solid part (cell wall) of cellulose that delimits a hollow part (lumen). Generally, the measurement of the fineness/maturity of the cotton fibers obtained with flow meter methods is accompanied by the so-called combined fineness and maturity index known in the industry as Micronaire.

As stated above, the measuring device 600 operates with flow rate measurement method, wherein a known quantity of fibers is enclosed in a measurement chamber of known dimensions and crossed by a flow of air, the fineness and maturity of the fiber being determined indirectly from the pressure drops at the ends of the measuring chambers due to the resistance that the fibers oppose to the flow of air that crosses the measurement chamber. Said measuring device 600 can operate at constant pressure or at constant flow.

The measuring device 600 comprises a support frame 601 whereon a measuring chamber CM is mounted, which is formed by a hollow cylinder 602, the axially opposite ends of which are open. The hollow cylinder 602 is mounted on the frame 601 in a movable manner among an insertion station S1, at which a known fiber sample is inserted in the measurement chamber CM, a measurement station S2, at which the measurements are carried out on the sample inserted in the measurement chamber CM, and an extraction station S3, at which, at the end of the measurements, the fiber sample is extracted from the measurement chamber CM. In the embodiment shown in the enclosed figures, the hollow cylinder 602 is mounted on a carousel 603 rotatable about a rotation axis, the insertion station S1, the measurement station S2 and the extraction station S3 being defined along the circular path made by the hollow cylinder 602. The carrousel 603 is mounted between a pair of plates 630a and 630b facing and parallel to one another, which are crossed by a plurality of openings adapted to be put in communication with the open ends of the hollow cylinder 602 and at which the three operating stations S1, S2 and S3 are defined.

The insertion station S1 comprises a feeding conduit 604 for feeding the cotton fibers into the hollow cylinder 602; these cotton fibers are sucked from the outlet of the measuring device 200 for the measurement of stickiness and can be preventively weighed. The insertion station S1 also comprises a pair of first pistons that are aligned and opposite one another and can be inserted into the opposite ends of the hollow cylinder 602. These first pistons are actuated by a respective first linear actuator 605a, 605b between a protracted position in the hollow cylinder 602 to compact the fiber sample inserted therein and a retracted position outside the hollow cylinder 602.

The feeding conduit 604 and one of the two first pistons communicate with a same open end of the hollow cylinder 602 by means of a junction 607 fixed to the frame 601.

The measurement station S2 comprises a pair of second pistons, aligned and opposite one another and insertable into the opposite ends of the hollow cylinder 602 to form respectively a first base and a second base. These second pistons and, consequently, the first base and the second base formed thereby, are of the permeable to air type; for example, they can be of the perforated type with calibrated holes. The second pistons are actuated by a respective second linear actuator 608A and 60B between at least one protracted position in the hollow cylinder 602 and a retracted position outside the hollow cylinder 602. A feeding conduit 609 (only shown schematically in FIG. 11) feeds a flow of air into the hollow cylinder 602 through the second piston that defines the first base. The flow of air fed into the hollow cylinder 602 exits therefrom through its second base that communicates with the external environment at ambient pressure.

The feeding conduit 609 has an inlet end associable with a source of air flow (not shown) and one outlet end associated with a pipe union 610 with which the second piston is associated, which defines the first base of the hollow cylinder 602.

Along the feeding conduit 609 a flow regulator 611 is positioned interposed between the inlet end and the outlet end of the feeding conduit 609 itself. The flow regulator 611 is, for example, formed by a throttle valve of the known type.

Along the feeding conduit 609 two pressure sensors are then located: a first pressure sensor 612 to detect air pressure that is positioned upstream of the flow regulator 611 and a second pressure sensor 613 to detect air pressure that is positioned downstream of the flow regulator 611 and upstream of the first base of the measurement chamber CM.

Advantageously, moreover, an electronic proportional pressure regulator 614 is positioned along the feeding conduit 609 upstream of the first pressure sensor 612 to regulate the air pressure in the feeding conduit 609.

The first pressure sensor 612, the second pressure sensor 613 and the electronic proportional pressure regulator 614 are connected to an electronic processing and control unit 615 that is programmed to control the electronic proportional pressure regulator 614 according to the detections of the first pressure sensor 612 and of the second pressure sensor 613 or of the second pressure sensor 613 alternatively and respectively to maintain substantially constant and equal to a pre-determinable value the difference between the pressure of the air upstream and downstream of the flow regulator 611 or the pressure of the air entering the measurement chamber CM. It is thus possible to operate in conditions of substantially constant flow or substantially constant pressure at the ends of the measurement chamber CM as required by the ASTM D1448-11 standard for the execution of fineness and maturity measurements, from which the Micronaire index is then obtained.

The electronic proportional pressure regulator 614 is selectively and alternatively controlled by the unit 615 to keep substantially constant and equal to a pre-set value the pressure difference upstream and downstream of the flow regulator 611, in order to operate in condition of substantially constant flow.

Or, the electronic proportional pressure regulator 614 is selectively and alternatively controlled by the unit 615 to keep substantially constant and equal to a pre-set value the pressure at the ends of the measurement chamber CM and, hence, the pressure entering said measurement chamber CM.

It is thus possible to operate under effective conditions of constant air flow or of pressure at the ends of the measurement chamber CM constant and equal to a pre-set value.

In fact, it is noted that at the measurement chamber S2, the second base of the hollow cylinder 602 communicates with the external environment, so that the values detected by the second pressure sensor 613 relate to the atmospheric pressure and provide a measurement of the pressure at the ends of the measurement chamber CM.

The extraction station S3 comprises a third piston, insertable into one of the two opposite ends of the hollow cylinder 602. The third piston is actuated by a respective third linear actuator 616 that is movable between a retracted position outside the hollow cylinder 602 and a protracted position inside the hollow cylinder 602 to push the fibers contained therein in order for them to exit from the open opposite end thereof. This makes the extraction of the fibers from the measurement chamber CM particularly simple.

The fibers expelled from the hollow cylinder 602 fall onto a scale 617 that measures their weight.

The operation of the measuring device 600 is immediately comprehensible to the skilled person from the above description and the enclosed figures.

Briefly, the carrousel 603 brings the hollow cylinder 602 at the insertion station S1 where the cylinder is filled with a known quantity of fibers, which are compacted by means of the first pistons.

The carousel 603 brings the hollow cylinder 602 thus filled in at the measuring station S2, at which the measurements of the pressure drop at the ends of the measurement chamber CM crossed by an air flow are carried out according to known protocols. These measures, which can be repeated on the same sample under different compaction conditions, can be carried out in conditions of substantially constant flow or of substantially constant pressure.

The carousel 603 then brings the hollow cylinder 602 at the extraction station S3, at which the sample is pushed out of the hollow cylinder 602 by the pushing action exercised thereon by the third piston. The sample falls onto the plate of the scale 617 and is weighed.

The measurements thus carried out are then processed through known algorithms in order to determine the fineness, maturity and the Micronaire index.

The method and the device for measuring the moisture content, the length and at least one dynamometric characteristic of textile fibers, in particular, cotton fibers, thus conceived can be subjected to numerous modifications and variations, all falling within the scope of the invention; in addition, all details can be replaced by technical equivalent elements. In practice, the materials used, as well as the dimensions, can be any according to the technical needs.

The invention claimed is:

1. A measuring device for measuring the moisture content, the length and/or at least one dynamometric characteristic of textile fibers, wherein said device comprises a housing in which a preparation area and a measuring area are defined and with which the following are associated:
   a perforated plate and a pressure plate that are arranged in said preparation area, are opposite one another and relatively movable with respect to one another for pressing a layer of textile fibers between them,
   a comb for withdrawing from said layer a line of textile fibers arranged substantially parallel and coplanar to one another, wherein said comb is movable between said preparation area and said measuring area,
   at least one measuring means selected from
   measuring means for measuring the length of the textile fibers of said line of textile fibers, said measuring means being arranged in said measuring area,
   and
   dynamometer means for measuring at least one dynamometric characteristic of the textile fibers of said line of textile fibers, said dynamometer means being arranged in said measuring area and
   extraction means for extracting textile fibers of said line of textile fibers from said measuring area,
   wherein said device is characterized in that it comprises measuring means for measuring the moisture content of the textile fibers forming said layer and/or forming said line of textile fibers, said measuring means for measuring the moisture content of the textile fibers being respectively placed at said preparation area and/or in said measuring area and/or being associated with said extraction means and comprising at least one microwave sensor for measuring moisture,
wherein at least one microwave sensor for measuring moisture is placed at said preparation area and is coupled to said pressure plate for measuring the moisture content of the fibers of said layer of fibers pressed between said pressure plate and said perforated plate.

2. A measuring device according to claim 1, wherein at least one microwave sensor for measuring moisture is placed at said preparation area and is configured to measure the moisture content of the fibers of said line of textile fibers withdrawn from said layer by means of said comb.

3. A measuring device according to claim 1, wherein the at least one measuring means comprises said dynamometer means, wherein at least one microwave sensor for measuring moisture is placed at said measuring area and upstream of said dynamometer means and is configured to measure the moisture content of the fibers of said line of textile fibers.

4. A measuring device according to claim 1, wherein the at least one measuring means comprises said dynamometer means, wherein at least one microwave sensor for measuring moisture is placed at said measuring area and downstream of said dynamometer means and is configured to measure the moisture content of the fibers of said line of textile fibers.

5. A measuring device according to claim 1, wherein the at least one microwave sensor for measuring moisture is associated with said extraction means.

6. A measuring device according to claim 1, wherein the extraction means includes a conduit having an end in communication with said measuring area and an end couplable with suction means, wherein said at least one microwave sensor for measuring moisture is of the tubular type and is placed along a section of said conduit.

7. A modular apparatus for measuring a plurality of characteristics of textile fibers, said apparatus comprising:
a plurality of modules each comprising at least one measuring device for measuring at least one characteristic of said textile fibers and a central processing and control unit for controlling said modules, one of said modules comprising a measuring device according claim 1.

8. A measuring device for measuring the moisture content, the length and/or at least one dynamometric characteristic of textile fibers, wherein said device comprises a housing in which a preparation area and a measuring area are defined and with which the following are associated:
a perforated plate and a pressure plate that are arranged in said preparation area, are opposite one another and relatively movable with respect to one another for pressing a layer of textile fibers between them,
a comb for withdrawing from said layer a line of textile fibers arranged substantially parallel and coplanar to one another, wherein said comb is movable between said preparation area and said measuring area,
at least one measuring means selected from
measuring means for measuring the length of the textile fibers of said line of textile fibers, said measuring means being arranged in said measuring area, and
dynamometer means for measuring at least one dynamometric characteristic of the textile fibers of said line of textile fibers, said dynamometer means being arranged in said measuring area and
extraction means for extracting textile fibers of said line of textile fibers from said measuring area,
wherein said device is characterized in that it comprises measuring means for measuring the moisture content of the textile fibers forming said layer and/or forming said line of textile fibers, said measuring means for measuring the moisture content of the textile fibers being respectively placed at said preparation area and/or in said measuring area and/or being associated with said extraction means and comprising at least one microwave sensor for measuring moisture,
wherein the at least one measuring means comprises said dynamometer means, wherein at least one microwave sensor for measuring moisture is placed at said measuring area and upstream of said dynamometer means and is configured to measure the moisture content of the fibers of said line of textile fibers.

9. The measuring device according to claim 8, wherein at least one microwave sensor for measuring moisture is placed at said preparation area and is coupled to said pressure plate for measuring the moisture content of the fibers of said layer of fibers pressed between said pressure plate and said perforated plate.

10. The measuring device according to claim 8, wherein at least one microwave sensor for measuring moisture is placed at said preparation area and is configured to measure the moisture content of the fibers of said line of textile fibers withdrawn from said layer by means of said comb.

11. The measuring device according to claim 8, wherein the at least one measuring means comprises said dynamometer means, wherein at least one microwave sensor for measuring moisture is placed at said measuring area and downstream of said dynamometer means and is configured to measure the moisture content of the fibers of said line of textile fibers.

12. The measuring device according to claim 8, wherein the at least one microwave sensor for measuring moisture is associated with said extraction means.

13. A measuring device according to claim 8, wherein the extraction means includes a conduit having an end in communication with said measuring area and an end couplable with suction means, wherein said at least one microwave sensor for measuring moisture is of the tubular type and is placed along a section of said conduit.

14. A modular apparatus for measuring a plurality of characteristics of textile fibers, the apparatus comprising:
a plurality of modules each comprising at least one measuring device for measuring at least one characteristic of said textile fibers and a central processing and control unit for controlling said modules,
wherein one of said modules comprises a measuring device according claim 8.

15. A measuring device for measuring the moisture content, the length and/or at least one dynamometric characteristic of textile fibers, wherein said device comprises a housing in which a preparation area and a measuring area are defined and with which the following are associated:
a perforated plate and a pressure plate that are arranged in said preparation area, are opposite one another and relatively movable with respect to one another for pressing a layer of textile fibers between them,
a comb for withdrawing from said layer a line of textile fibers arranged substantially parallel and coplanar to one another, wherein said comb is movable between said preparation area and said measuring area,
at least one measuring means selected from
measuring means for measuring the length of the textile fibers of said line of textile fibers, said measuring means being arranged in said measuring area,
and dynamometer means for measuring at least one dynamometric characteristic of the textile fibers of said line of textile fibers, said dynamometer means being arranged in said measuring area and extraction means for extracting textile fibers of said line of textile fibers from said measuring area, wherein said device is characterized in that it comprises measuring means for measuring the moisture content of the textile fibers forming said layer and/or forming said line of textile fibers, said measuring means for measuring the moisture content of the textile fibers being respectively placed at said preparation area and/or in said measuring area and/or being associated with said extraction means and comprising at least one microwave sensor for measuring moisture, wherein the at least one measuring means comprises said dynamometer means, wherein at least one microwave sensor for measuring moisture is placed at said measuring area and downstream of said dynamometer means and is configured to measure the moisture content of the fibers of said line of textile fibers.

16. The measuring device according to claim 15, wherein at least one microwave sensor for measuring moisture is placed at said preparation area and is coupled to said pressure plate for measuring the moisture content of the fibers of said layer of fibers pressed between said pressure plate and said perforated plate.

17. The measuring device according to claim 15, wherein at least one microwave sensor for measuring moisture is placed at said preparation area and is configured to measure the moisture content of the fibers of said line of textile fibers withdrawn from said layer by means of said comb.

18. The measuring device according to claim 15, wherein the at least one measuring means comprises said dynamometer means, wherein at least one microwave sensor for measuring moisture is placed at said measuring area and upstream of said dynamometer means and is configured to measure the moisture content of the fibers of said line of textile fibers.

19. The measuring device according to claim 15, wherein the at least one microwave sensor for measuring moisture is associated with said extraction means.

20. A measuring device according to claim 15, wherein the extraction means includes a conduit having an end in communication with said measuring area and an end couplable with suction means, wherein said at least one microwave sensor for measuring moisture is of the tubular type and is placed along a section of said conduit.

21. A modular apparatus for measuring a plurality of characteristics of textile fibers, the apparatus comprising:
a plurality of modules each comprising at least one measuring device for measuring at least one characteristic of said textile fibers and a central processing and control unit for controlling said modules,
wherein one of said modules comprises a measuring device according claim 15.

22. A measuring device for measuring the moisture content, the length and/or at least one dynamometric characteristic of textile fibers, wherein said device comprises a housing in which a preparation area and a measuring area are defined and with which the following are associated:
a perforated plate and a pressure plate that are arranged in said preparation area, are opposite one another and relatively movable with respect to one another for pressing a layer of textile fibers between them,
a comb for withdrawing from said layer a line of textile fibers arranged substantially parallel and coplanar to one another, wherein said comb is movable between said preparation area and said measuring area,
at least one measuring means selected from
measuring means for measuring the length of the textile fibers of said line of textile fibers, said measuring means being arranged in said measuring area,
and
dynamometer means for measuring at least one dynamometric characteristic of the textile fibers of said line of textile fibers, said dynamometer means being arranged in said measuring area and
extraction means for extracting textile fibers of said line of textile fibers from said measuring area,
wherein said device is characterized in that it comprises measuring means for measuring the moisture content of the textile fibers forming said layer and/or forming said line of textile fibers, said measuring means for measuring the moisture content of the textile fibers being respectively placed at said preparation area and/or in said measuring area and/or being associated with said extraction means and comprising at least one microwave sensor for measuring moisture,
wherein the at least one microwave sensor for measuring moisture is associated with said extraction means, and
wherein the extraction means includes a conduit having an end in communication with said measuring area and an end couplable with suction means, wherein at least one microwave sensor for measuring moisture is of the tubular type and is placed along a section of said conduit.

23. The measuring device according to claim 22, wherein at least one microwave sensor for measuring moisture is placed at said preparation area and is coupled to said pressure plate for measuring the moisture content of the fibers of said layer of fibers pressed between said pressure plate and said perforated plate.

24. The measuring device according to claim 22, wherein at least one microwave sensor for measuring moisture is placed at said preparation area and is configured to measure the moisture content of the fibers of said line of textile fibers withdrawn from said layer by means of said comb.

25. The measuring device according to claim 22, wherein the at least one measuring means comprises said dynamometer means, wherein at least one microwave sensor for measuring moisture is placed at said measuring area and upstream of said dynamometer means and is configured to measure the moisture content of the fibers of said line of textile fibers.

26. The measuring device according to claim 22, wherein the at least one measuring means comprises said dynamometer means, wherein at least one microwave sensor for measuring moisture is placed at said measuring area and downstream of said dynamometer means and is configured to measure the moisture content of the fibers of said line of textile fibers.

27. A modular apparatus for measuring a plurality of characteristics of textile fibers, the apparatus comprising:
a plurality of modules each comprising at least one measuring device for measuring at least one characteristic of said textile fibers and a central processing and control unit for controlling said modules,
wherein one of said modules comprises a measuring device according claim 22.

* * * * *